United States Patent
Daluge

(10) Patent No.: US 6,630,477 B1
(45) Date of Patent: Oct. 7, 2003

(54) THERAPEUTIC NUCLEOSIDE COMPOUND

(75) Inventor: Susan Mary Daluge, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/913,309

(22) PCT Filed: Feb. 11, 2000

(86) PCT No.: PCT/GB00/00429

§ 371 (c)(1),
(2), (4) Date: Oct. 12, 2001

(87) PCT Pub. No.: WO00/47581

PCT Pub. Date: Aug. 17, 2000

(30) Foreign Application Priority Data

Feb. 12, 1999 (GB) .............................................. 9903091

(51) Int. Cl.⁷ .............................................. A61K 31/52

(52) U.S. Cl. ........................ 514/261; 514/931; 514/934
(58) Field of Search .......................................... 514/261

(56) References Cited

U.S. PATENT DOCUMENTS 4,916,224 A    4/1990   Vince et al.

FOREIGN PATENT DOCUMENTS

| EP | 0346132 A1 | * 12/1989 | .......... A61K/31/70 |
|----|------------|-----------|----------------------|
| EP | 0349242 A  | 1/1990    |                      |
| EP | 0366385 A  | 5/1990    |                      |
| EP | 0434450 A  | 6/1991    |                      |
| WO | WO96 06844 A | 3/1996  |                      |

* cited by examiner

Primary Examiner—T J Criares
(74) Attorney, Agent, or Firm—Karen L. Prus

(57) ABSTRACT

The present invention relates to (1R,4S)-4-(6-amino-9H-purin-9-yl)-2-cyclopentene-1-methanol and its use in medical therapy for the treatment of hepatitis B infection.

2 Claims, No Drawings

THERAPEUTIC NUCLEOSIDE COMPOUND

This application is filed pursuant to 35 U.S.C. §371 as a United States National Phase Application of International Application No. PCT/GB00/00429 filed Feb. 11, 2000 which claims priority from GB9903091.8 filed Feb. 12, 1999 in the United Kingdom.

FIELD OF THE INVENTION

The present invention relates to (1R,4S)-4-(6-amino-9H-purin-9-yl)-2-cyclopentene-1-methanol and its use in medical therapy.

BACKGROUND OF THE INVENTION

Hepatitis B virus (HBV) is a small DNA containing virus which infects humans. It is a member of the class of closely related viruses known as the hepadnaviruses, each member of which selectively infects either mammalian or avian hosts, such as the woodchuck and the duck. Recent insights into the mechanism of replication of the hepadnavirus genome indicate the importance of reverse transcription of an RNA intermediate, suggesting that the reverse transcriptase is a logical chemotherapeutic target. HBV is a viral pathogen of major worldwide importance. The virus is etiologically associated with primary hepatocellular carcinoma and is thought to cause 80% of the world's liver cancer. Clinical effects of infection with HBV range from headache, fever, malaise, nausea, vomiting, anorexia and abdominal pains. Replication of the virus is usually controlled by the immune response, with a course of recovery lasting weeks or months in humans, but infection may be more severe leading to persistent chronic liver disease outlined above.

U.S. Pat. No. 4,916,224 discloses dideoxycarbocyclic nucleosides and their use in the treatment of HIV. Wang et al. (*Bioorganic Et Medicinal Chemistry Letters* 8, pp. 1585–1588, 1998) disclose the synthesis of L-carbocyclic 2',3'-didehydro-2',3'-dideoxyadensosine and its use in HIV infections.

SUMMARY OF THE INVENTION

An aspect of the present invention relates to the use of (1R,4S)-4-(6-amino-9H-purin-9-yl)-2-cyclopentene-1-methanol in the treatment of Hepatitis B infections.

DETAILED DESCRIPTION OF THE INVENTION

The present invention features compounds of formula (I)

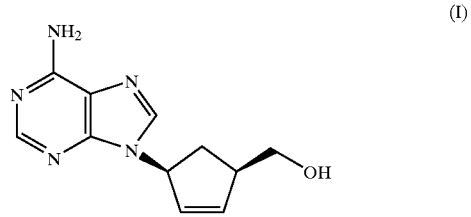

also known as (1R,4S)-4-(6-amino-9H-purin-9-yl)-2-cyclopentene-1-methanol and pharmaceutically acceptable salts thereof for the prophylaxis and treatment of Hepatitis B infections.

Physiologically acceptable salts of (1R,4S)-4-(6-amino-9H-purin-9-yl)-2-cyclopentene-1-methanol include salts of organic carboxylic acids such as acetic, lactic, tartaric, malic, isethionic, lactobionic, and succinic acids, organic sulphonic acids, such as methanesulphonic, ethanesulphonic, benzenesulphonic and p-toluenesulphonic acids and inorganic acids, such as hydrochloric, sulphuric, phosphoric and sulphamic acids. For therapeutic use, salts of (1R,4S)-4-(6-amino-9H-purin-9-yl)-2-cyclopentene-1-methanol will be physiologically acceptable, i.e. they will be salts derived from a physiologically acceptable acid. However, salts of acids which are not physiologically acceptable may also find use, for example, in the preparation or purification of a physiologically acceptable compound. All salts, whether or not derived from a physiologically acceptable acid, are within the scope of the present invention. A preferred salt of (1R,4S)-4-(6-amino-9H-purin-9-yl)-2-cyclopentene-1-methanol is the succinate salt. (1R,4S)-4-(6-amino-9H-purin-9-yl)-2-cyclopentene-1-methanol may be synthesized by the known 3-step sequence (see, e.g., Y. F. Shealy and J. D. Clayton, *J. Amer. Chem. Soc.* 1969, 91: 3075–3887 and references therein) involving the condensation of (1S,4R)-4-amino-2-cyclopentene-1-methanol or a salt thereof (4) with 5-amino-6-chloropyrimidine

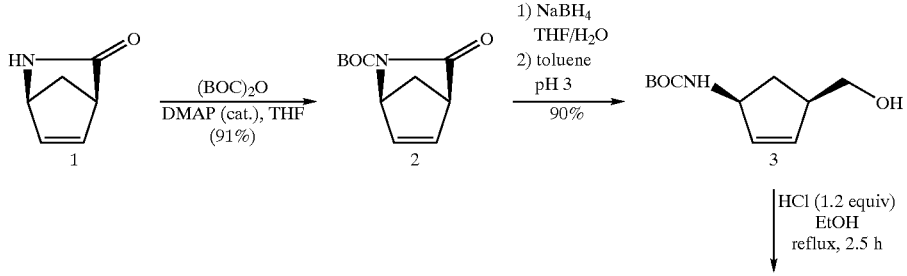

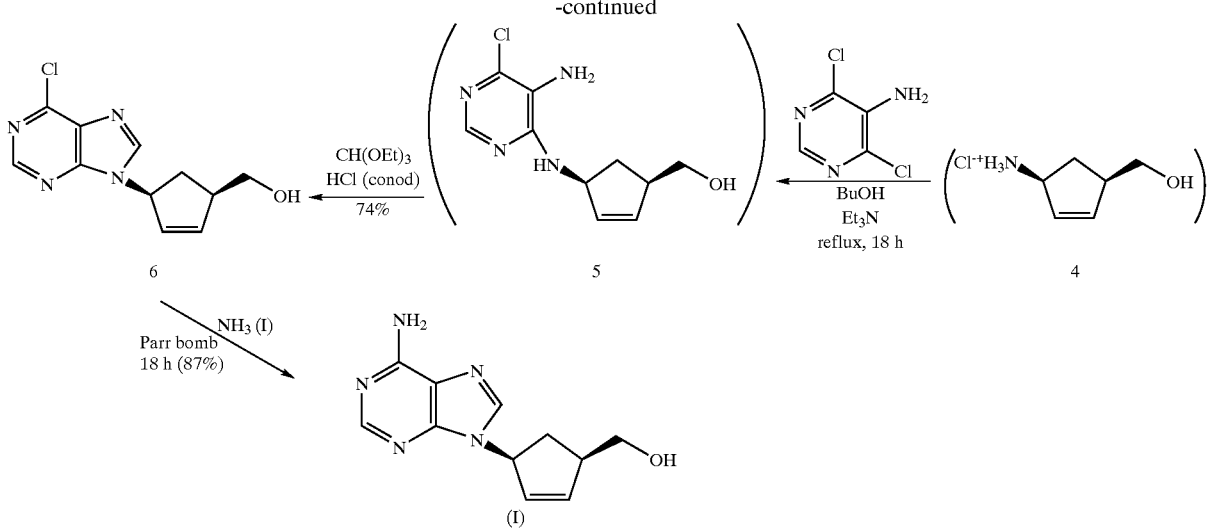

in refluxing n-butanol in the presence of an excess of a non-nucleophilic base, e.g. triethylamine. The resulting pyrimidine intermediate (5) may be converted to the 6-chloropurine intermediate (6) by triethylorthoformate in the presence of a catalytic amount of acid. Amination of (6) with ammonia may provide (I) in good yield and purity.

(1S,4R)-4-amino-2-cyclopentene-1-methanol may be synthesized in 3 steps from (+)-2-azabicyclo[2.2.1]hept-5-en-3-one, for example, as in Example 1.

In one aspect of the present invention there is provided (1R,4S)-4-(6-amino-9H-purin-9-yl)-2-cyclopentene-1-methanol, or a pharmaceutically acceptable salt thereof for use in medical therapy, particularly for the treatment of hepatitis B virus infections.

The present invention features a method for the treatment of a hepatitis B virus infection in a host comprising administering to said host a therapeutically effective amount of (1R,4S)-4-(6-amino-9H-purin-9-yl)-2-cyclopentene-1-methanol or a pharmaceutically acceptable salt thereof. Preferably the host is a human.

Another aspect of the present invention features the use of (1R,4S)-4-(6-amino-9H-purin-9-yl)-2-cyclopentene-1-methanol or a pharmaceutically acceptable salt thereof in the manufacture of a medicament for the treatment or prevention of a hepatitis B virus infection.

(1R,4S)-4-(6-amino-9H-purin-9-yl)-2-cyclopentene-1-methanol, also referred to herein as the active ingredient, may be administered for therapy by any suitable route including oral, rectal, nasal, topical (including buccal and sublingual), vaginal and parenteral (including subcutaneous, intramuscular, intravenous and intradermal). It will be appreciated that the preferred route will vary with the condition and age of the recipient, the nature of the infection and the chosen active ingredient.

The amounts required of the active ingredient will depend upon a number of factors including the severity of the condition to be treated and the identity of the recipient and will ultimately be at the discretion of the attendant physician or veterinarian. In general however, for each of these utilities and indications, a suitable effective dose of a compound of formula (I) will be in the range of 0.01 to 100 mg per kilogram body weight of recipient per day, advantageously in the range of 1 to 70 mg per kilogram body weight per day, preferably in the range of 1 to 50 mg per kilogram body weight per day.

The desired dose is preferably presented as one, two, three or four or more subdoses administered at appropriate intervals throughout the day. These sub-doses may be administered in unit dosage forms, for example, containing about 25 to 2000 mg, preferably about 25, 50, 100, 150, 200, or 250 mg of active ingredient per unit dose form.

While it is possible for the active ingredient to be administered alone, it is preferable to present it as a pharmaceutical composition. A further aspect of the present invention features pharmaceutical compositions comprising (1R,4S)-4-(6-amino-9H-purin-9-yl)-2-cyclopentene-1-methanol or a pharmaceutically acceptable salt thereof and a pharmaceutically acceptable carrier therefor.

The compositions of the present invention comprise at least one active ingredient, as defined above, together with one or more pharmaceutically acceptable carriers thereof and optionally other therapeutic agents. Each carrier must be "acceptable" in the sense of being compatible with the other ingredients of the composition and not deleterious to the recipient thereof. Compositions include those suitable for oral, rectal, nasal, topical (including buccal and sublingual), vaginal or parenteral (including subcutaneous, intramuscular, intravenous and intradermal) administration.

The compositions of the present invention may conveniently be presented in unit dosage form prepared by any of the methods well known in the art of pharmacy. Such methods include the step of bringing into association the active ingredient with the carrier which constitutes one or more accessory ingredients. In general, the compositions are prepared by uniformly and intimately bringing in to association the active ingredient with liquid carriers or finely divided solid carriers or both, and then, if necessary, shaping the product.

Compositions of the present invention suitable for oral administration may be presented as discrete units such as capsules, cachets, sachets of granules or tablets (such as a swallowable, dispersible or chewable tablet) each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Moulded tablets may be made by moulding in a suitable machine a mixture of the powdered compound moistened with an inert liquid diluent. The tablets may optionally be coated or scored any may be formulated so as to provide slow or controlled release of the active ingredient therein.

Compositions suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Compositions for rectal administration may be presented as a suppository with a suitable base comprising for example cocoa butter or a salicylate.

Compositions suitable for vaginal administration may be presented as pessaries, tampons, creams, gels, pastes, foams or spray formulations containing in addition to the active ingredient such carriers as are known in the art to be appropriate.

Compositions suitable for parenteral administration include aqueous and non-aqueous isotonic sterile injection solution which may contain anti-oxidants, buffers, bacteriostats and solutes which render the formulation aqueous and non-aqueous sterile suspensions which may include suspending agents and thickening agents. The compositions may be presented in unit-dose or multidose sealed containers, for example, ampoules and vial, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

The active ingredient may also be presented in a composition comprising micrometer- or nanometer-size particles of active ingredient.

Preferred unit dosage compositions are those containing a daily dose or unit daily sub-dose (as herein above recited) or an appropriate fraction thereof, of the active ingredient.

It should be understood that in addition to the ingredients particularly mentioned above the composition of this invention may include other agents conventional in the art having regard to the type of formulation in question, for example those suitable for oral administration may include flavoring agents or taste masking agents.

A further aspect of the invention relates to kits to be used in the treatment of patients suffering from viral infections. These kits include one or more oral dosage of a compound of formula (I) and may include one or more additional therapeutic agents. By way of illustration, a kit of the invention may include one or more tablets, capsules, caplets, gelcaps or liquid formulations containing a compound of formula (I) and one or more tablets, capsules, caplets, gelcaps or liquid formulations containing a compound of formula (I) in dosage amounts within the ranges described above. The kits may include as an insert printed dosing information for the co-administration of the agents.

The active ingredient may also be presented in a composition comprising micrometer- or nanometer-size particles of active ingredient.

(1R,4S)-4-(6-amino-9H-purin-9-yl)-2-cyclopentene-1-methanol may be administered with other therapeutic agents. Other therapeutic agents may include agents that are effective for the treatment of viral infections or associated conditions such as nucleoside reverse transcriptase inhibitors, for example, zidovudine or abacavir, 2',3'-dideoxycytidine, 2',3'-dideoxyadenosine, 2',3'-dideoxyinosine, 2',3'-didehydrothymidine; (1 alpha, 2 beta, 3 alpha)-9-[2,3-bis(hydroxymethyl)cyclobutyl]guanine [(−) BHCG, SQ-34514]; oxetanocin-G (3,4-bis-(hydroxymethyl)-2-oxetanosyl]guanine); acyclic nucleosides (e.g. acyclovir, valaciclovir, famciclovir, ganciclovir, penciclovir); acyclic nucleoside phosphonates (e.g. (S)-1-(3-hydroxy-2-phosphonyl-methoxypropyl)cytosine (HPMPC) or PMEA; protease inhibitors such as indinavir, ritonavir, nelfinavir, amprenavir, sanquinavir; oxathiolane nucleoside analogues such as lamivudine, cis-1-(2-(hydroxymethyl)-1,3-oxathiolan-5-yl)-5-fluorocytosine (FTC), ribavirin, 9-[4-hydroxy-2-(hydroxymethyl)but-1-yl]-guanine (H2G), dioxolane G, L-FMAU; tat inhibitors such as 7-chloro-5-(2-pyrryl)-3H-1,4-benzodiazepin-2-(H)one (Ro5-3335), 7-chloro-1,3-dihydro-5-(1H-pyrrol-2yl)-3H-1,4-benzodiazepin-2-amine (Ro24-7429); interferons such as a-interferon; renal exeretion inhibitors such as probenecid, nucleoside transport inhibitors such as dipyridamole; pentoxifylline, N-acetylcysteine (NAC), Procysteine, α-trichosanthin, phosphonoformic acid, as well as immunomodulators such as interleukin II or thymosin, granulocyte macrophage colony stimulating factors, erythropoetin, soluble $CD_4$ and genetically engineered derivatives thereof; or non-nucleoside reverse transcriptase inhibitors (NNRTIs) such as nevirapine (BI-RG-587), loviride (α-APA) and delavuridine (BHAP), and phosphonoformic acid, and 1,4-dihydro-2H-3,1-benzoxazin-2-ones NNRTIs such as (−)-6-chloro-4-cyclopropylethynyl-4-trifluoromethyl-1,4-dihydro-2H-3,1-benzoxazin-2-one (L-743,726 or DMP-266), and quinoxaline NNRTIs such as isopropyl (2S)-7-fluoro-3,4-dihydro-2-ethyl-3-oxo-1 (2H)-quinoxalinecarboxylate (HBY1293). The therapeutic agents, including (1R,4S)-4-(6-amino-9H-purin-9-yl)-2-cyclopentene-1-methanol may be administered concurrently, sequentially, or as part of the same composition.

The following examples are intended for illustration only and are not intended to limit the scope of the invention in any way.

EXAMPLE 1

(+)-(1R,4S)-4-(6-Amino-9H-purin-9-yl)-2-cyclopentene-1-methanol (a) (1S,4R)-tert-Butyl 3-oxo-2-Azabicyclo[2.2.1]hept-5-ene-2-carboxylate (+)-2-Azabicyclo[2.2.1]hept-5-en-3-one (Chiroscience, Cambridge, England; 54.565 g, 0.500 mole) was dissolved in dry tetrahydrofuran (350 mL). Di-tert-butyl carbonate (Aldrich, 114.87 g, 0.510 mole as 97%) and 4-dimethylaminopyridine (Aldrich, 600 mg) were added to the stirred mixture. The resulting solution was stirred at ambient temperature for 2 hours. Solvent was evaporated under reduced pressure and the residual orange solid was crystallized from toluene-hexanes to give title compound as white crystals (95.72 g, 91%), m.p. 85–86° C.; $^1$H-NMR ($CDCl_3$) δ: 1.50 (s, 9H), 2.24 (app AB q, J=8.4 Hz, 2H), 3.39 (br s, 1H), 4.96 (m, 1H), 6.66 (m, 1H), 6.89 (m, 1H).

Anal. Calcd. For $C_{11}H_{15}NO_3$: C, 63.14; H, 7.21; N, 6.69. Found: C, 63.20; H, 7.26; N, 6.65.

(b) (+)-(1S,4R)-tert-Butyl N-[4-(Hydroxymethyl)-2-cyclopenten-1-yl]carbamate

A solution of (1S,4R)-tert-butyl 3-oxo-2-azabicyclo[2.2.1]hept-5-ene-2-carboxylate (part a of this example, 95.50 g, 0.456 mole) in tetrahydrofuran (500 mL)-water (50 mL) was added over 10 minutes to a vigorously stirred solution of sodium borohydride (Aldrich, 21.96 g, 0.580 mole as 99%) in water (100 mL). The temperature was maintained below 35° C. After 2 hours, the solution was cooled to maintain the temperature below 25° C. while concentrated hydrochloric acid (50 mL) was added over 10 minutes. Additional water (100 mL) was added to dissolve solid and the solution was extracted with toluene (4×300 mL). The combined organic layers were washed with 9:1 saturated sodium sulfate/saturated sodium carbonate (200 mL) and dried (sodium sulfate).

Evaporation of solvents under reduced pressure left a colorless syrup which crystallized on stirring with hexanes (200 mL) to provide title compound as a fine white powder (87.16 g, 90%), m.p. 72–73° C.; $^1$H-NMR (DMSO-d$_6$) δ: 6.78 (d, J=7.6 Hz, 1H), 5.80 and 5.60 (two m, 2H), 4.58 (t, J=5.25 Hz, 2H), 4.45 (m, 1H), 3.35 (m overlapping water), 2.60 (m, 1H), 2.30 (m, 1 H), 1.38 (s, 9H), 1.20 (m, 1 H); $[α]_{589}$+2.80° (c 5.0, methanol).

Anal. Calcd. for $C_{11}H_{19}NO_3$: C, 61.95; H, 8.98; N, 6.57. Found: C, 61.87; H, 8.97; N, 6.55.

(c) (+)-(1R,4S)-4-Amino-2-cyclopentene-1-methanol Hydrochloride (+)-(1S,4R)-tert-Butyl N-[4-(hydroxymethyl)-2-cyclopenten-1-yl]carbamate (part b of this example, 10.66 g, 50.0 mmol) was refluxed in absolute ethanol (25 mL) with concentrated hydrochloric acid (5.0 mL, 60 mequiv) for 2.5 hours. Evaporation of volatiles left title compound as white solid; mass spectrum (ES): 114 (M+1); $^1$H-NMR (DMSO-d$_6$) δ: 7.9 (m, 3H), 6.03 and 5.75 (two m, 2H), 4.11 (m, 1H), 3.41 (d, J=5.4 Hz, 2H), 2.8 (m, 1H), 2.36 (m, 1H), 1.4 (m, 1H). This solid was used immediately in the following example.

(d) (1R,4S)-4-[(5-Amino-6-chloro-4-pyrimidinyl)amino]-2-cyclopentene-1-methanol

A solution of (+)-(1S,4R)-4-amino-2-cyclopentene-1-methanol hydrochloride (from deblocking of 10.66 g, 50.0 mmoles of (+)-(1S,4R)-tert-butyl N-[4-(hydroxymethyl)-2-cyclopenten-1-yl]carbamate as described in part c of this example), 5-amino-4,6-dichloropyrimidine (Aldrich, 16.40 g, 0.100 mole), and triethylamine (15.2 g, 0.150 mole) in 1-butanol (25 mL) was refluxed under nitrogen for 18 hours. The solution was cooled and 1 N sodium hydroxide (100 mL) added. Volatiles were evaporated under reduced pressure and the residual solid was chromatographed on silica gel. Title compound eluted with 5% methanol-chloroform as a pale yellow glass (10.8 g). Crystallization of such a sample from ethyl acetate gave title compound as white needles, m.p. 151–154° C.; $^1$H-NMR (DMSO-d$_6$) δ: 7.75 (s, 1H), 6.76 (d, J=6.8 Hz, 1H), 5.93 and 5.82 (two m, 2H), 5.11 (m, 3H), 4.66 (t, J=5.3 Hz, 1H), 3.40 (br t, J=6.1 Hz, 2H), 2.75 (m, 1H), 2.20 (m, 1H), 1.38 (m, 1H).

(e) (1R,4S)-4-(6-Chloro-9H-purin-9-yl)-2-cyclopentene-1-methanol (1R,4S)-4-[(5-Amino-6-chloro-4-pyrimidinyl) amino]-2-cyclopentene-1-methanol (from part d of this example, 9.63 g, 40.0 mmol), triethylorthoformate (150 mL), and concentrated hydrochloric acid (14 mL) were stirred for 3 hours. Volatiles were evaporated and the residual solid was partitioned between chloroform (300 mL) and saturated aqueous sodium carbonate (100 mL). The aqueous layer was extracted with chloroform (2×100 mL). The combined chloroform layers were dried (sodium sulfate). Volatiles were evaporated under reduced pressure and the residual yellow glass was chromatographed on silica gel. Elution with ethyl acetate gave title compound as white needles from ethyl acetate (7.45 g, 74%), m.p. 121–124° C.; $^1$H-NMR (DMSO-d$_6$) δ: 8.81 (s, 1H), 8.64 (s, 1H), 6.24 and 6.21 (two m, 2H), 5.75 (m, 1H), 4.75 (t, J=5.4 Hz, 1H), 3.34 (m, 2H), 2.95 (m, 1H), 2.75 (m, 1H), 1.75 (m, 1H).

Anal. Calcd. for $C_{11}H_{11}N_4ClO$: C, 52.70; H, 4.42; N, 22.35; Cl, 14.14. Found: C, 52.81; H, 4.46; N, 22.31; 14.22.

(f) (+)-(1R,4S)-4-(6-Amino-9H-purin-9-yl)-2-cyclopentene-1-methanol (1R,4S)-4-(6-Chloro-9H-purin-9-yl)-2-cyclopentene-1-methanol (from part e of this example, 2.00 g, 7.98 mmol) was stirred in liquid ammonia (50 mL) in a Parr bomb at 25° C. for 18 hours. Evaporation of volatiles and crystallization of the residual solid from methanol-acetonitrile gave title compound as white prisms (1.61 g, 87%), m.p. 195–200° C.; $^1$H-NMR (DMSO-d$_6$) δ: 8.15 (s, 1H), 8.06 (s, 1H), 7.21 (br s, 2H), 6.15 and 5.95 (two m, 2H), 5.61 (m, 1H), 4.76 (t, J=5.4 Hz, 1H), 3.48 (t, J=5.5 Hz, 2H), 2.92 (m, 1H), 2.71 (m, 1H), 1.67 (m, 1H ); $[α]_{589}$+4.5° (c 0.5, methanol).

Anal. Calcd. for $C_{11}H_{13}N_5O$: C, 57.13; H, 5.67; N, 30.28. Found: C, 57.25; H, 5.67; N, 30.33.

EXAMPLE 2

Hepatitis B Virus Activity

Method

The activity of compounds against Hepatitis B Virus was assessed as described in Jansen, R. et al., *Antimicrobial Agents and Chemotherapy*, Vol. 37, No. 3, pp. 441–447, 1993.

Results

The IC$_{50}$ for (+)-(1R,4S)-4-(6-Amino-9H-purin-9-yl)-2-cyclopentene-1-methanol against Hepatitis B virus was 1.0 μM (n=2). Cytotoxicity was found to be >200 μM.

EXAMPLE 3

Tablet Formulation

The following formulations A, B and C are prepared by wet granulation of the ingredients with a solution of povidone, followed by addition of magnesium stearate and compression.

| Formulation A | mg/tablet |
| --- | --- |
| Active Ingredient | 250 |
| Lactose B.P. | 210 |
| Povidone B.P. | 15 |
| Sodium Starch Glycollate | 20 |
| Magnesium Stearate | 5 |
| | 500 |

| Formulation B | mg/tablet |
| --- | --- |
| Active Ingredient | 250 |
| Lactose B.P. | 150 |
| Avicel PH 101 | 60 |
| Povidone B.P. | 15 |
| Sodium Starch Glycollate | 20 |
| Magnesium Stearate | 5 |
| | 500 |

| Formulation C | mg/tablet |
|---|---|
| Active Ingredient | 250 |
| Lactose B.P. | 200 |
| Starch | 50 |
| Povidone | 5 |
| Magnesium Stearate | 4 |
|  | 359 |

The following formulations, D and E, are prepared by direct compression of the admixed ingredients. The lactose in formulation E is of the direct compression type (Dairy Crest-"Zeparox").

| Formulation D | mg/tablet |
|---|---|
| Active Ingredient | 250 |
| Pregelatinized Starch NF15 | 150 |
|  | 400 |

| Formulation E | mg/tablet |
|---|---|
| Active Ingredient | 250 |
| Lactose B.P. | 50 |
| Avicel | 100 |
|  | 500 |

Formulation F (Controlled Release Formulation)

The formulation is prepared by wet granulation of the ingredients with a solution of povidone followed by the addition of magnesium stearate and compression.

|  | mg/tablet |
|---|---|
| Active Ingredient | 500 |
| Hydroxypropylmethylcellulose (Methocel K4M Premium) | 112 |
| Lactose B.P. | 53 |
| Povidone B.P. | 28 |
| Magnesium Stearate | 7 |
|  | 700 |

Drug release takes place over a period of about 6–8 hours and is complete after 12 hours.

Example 4

Capsule Formulations

Formulation A

A capsule formulation is prepared by admixing the ingredients of formulation D in Example 3 above and filling into a two-part hard gelatin capsule. Formulation B (infra) is prepared in a similar manner.

| Formulation B | mg/capsule |
|---|---|
| Active Ingredient | 250 |
| Lactose B.P. | 143 |
| Sodium Starch Glycollate | 25 |
| Magnesium Stearate | 2 |
|  | 420 |

| Formulation C | mg/capsule |
|---|---|
| Active Ingredient | 250 |
| Macrogel 4000 B.P. | 350 |
|  | 600 |

Capsules of formulation C are prepared by melting the Macrogel 4000 B.P., dispersing the active ingredient in the melt and filling the melt into a two-part hard gelatin capsule.

| Formulation D | mg/capsule |
|---|---|
| Active Ingredient | 250 |
| Lecithin | 100 |
| Arachis Oil | 100 |
|  | 450 |

Capsules of formulation D are prepared by dispersing the active ingredient in the lecithin and arachis oil and filling the dispersion into soft, elastic gelatin capsules.

| Formulation E | mg/capsule |
|---|---|
| Active Ingredient | 150.0 |
| Vitamin E TPGS | 400.0 |
| Polyethylene Glycol 400 NF | 200.5 |
| Propylene Glycol USP | 39.5 |

Four (4) kilograms (kg) of Vitamin E TPGS (obtained from Eastman Chemical Co.) was heated at 50° C. until liquefied. To the liquified Vitamin E TPGS, 2.005 kg of polyethylene glycol 400 (PEG400) (low aldehyde, <10 ppm, obtained from Union Carbide or Dow Chemical Co.) heated to 50° C. was added and mixed until a homogeneous solution was formed. The resultant solution was heated to 65° C. 1.5 kg of active ingredient was dissolved in the liquefied solution of Vitamin E TPGS and PEG 400. 0.395 kg of propylene glycol at room temperature was added and mixed until a homogenous solution was formed. The solution was cooled to 28–35° C. The solution was then de-gassed. The mixture was preferably encapsulated at 28–35° C. at a fill weight equivalent to 150 mg of volatiles-free compound, into Size 12 oblong, white opaque soft gelatin capsules using a capsule filling machine. The capsule shells were dried to a constant fill moisture of 3–6% water and a shell hardness of 7–10 Newtons, and placed in a suitable container.

Formulation F (Controlled Release Capsule)

The following controlled release capsule formulation is prepared by extruding ingredients a, b, and c using an extruder, followed by spheronization of the extrudate and drying. The dried pellets are then coated with release-controlling membrane (d) and filled into a two-piece, hard gelatin capsule.

|  | mg/capsule |
|---|---|
| (a) Active Ingredient | 250 |
| (b) Microcrystalline Cellulose | 125 |
| (c) Lactose B.P. | 125 |
| (d) Ethyl Cellulose | 13 |
|  | 513 |

EXAMPLE 5

Injectable Formulation

| Formulation A | mg |
|---|---|
| Active Ingredient | 200 |
| Hydrochloric Acid Solution 0.1M or Sodium Hydroxide Solution 0.1M q.s. to pH | 4.0 to 7.0 |
| Sterile water q.s. to | 10 ml |

The active ingredient is dissolved in most of the water (35°–40° C.) and the pH adjusted to between 4.0 and 7.0 with the hydrochloric acid or the sodium hydroxide as appropriate. The batch is then made up to volume with water and filtered through a sterile micropore filter into a sterile 10 ml amber glass vial (type 1) and sealed with sterile closures and overseals.

| Formulation B | |
|---|---|
| Active Ingredient | 125 mg |
| Sterile, Pyrogen-free, pH 7 Phosphate Buffer, q.s. to | 25 ml |

EXAMPLE 6

Intramuscular Injection

| Active Ingredient | 200 mg |
|---|---|
| Benzyl Alcohol | 0.10 g |
| Glycofurol 75 | 1.45 g |
| Water for injection q.s. to | 3.00 ml |

The active ingredient is dissolved in the glycofurol. The benzyl alcohol is then added and dissolved, and water added to 3 ml. The mixture is then filtered through a sterile micropore filter and sealed in sterile 3 ml amber glass vials (type 1).

EXAMPLE 7

Syrup

| Active ingredient | 250 mg |
|---|---|
| Sorbitol Solution | 1.50 g |
| Glycerol | 2.00 g |
| Sodium Benzoate | 0.005 g |
| Flavor, Peach 17.42.3169 | 0.0125 ml |
| Purified Water q.s. to | 5.00 ml |

The active ingredient is dissolved in a mixture of the glycerol and most of the purified water. An aqueous solution of the sodium benzoate is then added to the solution, followed by addition of the sorbital solution and finally the flavor. The volume is made up with purified water and mixed well.

EXAMPLE 8

Suppository

|  | mg/capsule suppository |
|---|---|
| Active Ingredient | 250 |
| Hard Fat, B.P. (Witepso H15-Dynamit Nobel) | 1770 |
|  | 2020 |

One-fifth of the Witepsol H15 is melted in a steam-jacketed pan at 45° C. maximum. The active ingredient is sifted through a 200 $\mu$m sieve and added to the molten base with mixing, using a Silverson fitted with a cutting head, until a smooth dispersion is achieved. Maintaining the mixture at 45° C., the remaining Witepsol H15 is added to the suspension and stirred to ensure a homogenous mix. The entire suspension is passed through a 250 $\mu$m stainless steel screen and, with continuous stirring, is allowed to cool to 45° C. At a temperature of 38° C. to 40° C., 2.02 g of the mixture is filled into suitable, 2 ml plastic molds. The suppositories are allowed to cool to room temperature.

EXAMPLE 9

Pessaries

|  | mg/pessary |
|---|---|
| Active Ingredient | 250 |
| Anhydrate Dextrose | 380 |
| Potato Starch | 363 |
| Magnesium Stearate | 7 |
|  | 1000 |

The above ingredients are mixed directly.

What is claimed is:

1. A method of treating a Hepatitis B virus infection in a human comprising administering to said human an effective anti-Hepatitis B treatment amount of (1R,4S)-4-(6-amino-9H-purin-9-yl)-2-cyclopentene-1-methanol or a pharmaceutically acceptable salt thereof.

2. A method of treatment according to claim 1 wherein the pharmaceutically acceptable salt is (1R,4S)-4-(6-amino-9H-purin-9-yl)-2-cyclopentene-1-methanol succinate salt.

* * * * *